United States Patent [19]

Bays et al.

[11] 4,450,168
[45] May 22, 1984

[54] PHARMACEUTICAL COMPOSITIONS CONTAINING COMPOUNDS HAVING ACTION ON HISTAMINE RECEPTORS

[75] Inventors: David E. Bays; Roger Hayes, both of Hertfordshire, England

[73] Assignee: Glaxo Group Limited, London, England

[21] Appl. No.: 513,750

[22] Filed: Jul. 14, 1983

Related U.S. Application Data

[63] Continuation of Ser. No. 401,152, Jul. 22, 1982, abandoned.

[30] Foreign Application Priority Data

Jul. 22, 1981 [GB] United Kingdom ............... 8122607

[51] Int. Cl.³ .................... A61K 31/44; C07D 403/12
[52] U.S. Cl. .................................. 424/267; 424/269; 546/210; 548/266
[58] Field of Search ...................... 546/210; 548/266; 424/267, 269

[56] References Cited

FOREIGN PATENT DOCUMENTS 2063253 6/1981 United Kingdom ............... 548/266

*Primary Examiner*—Robert T. Bond
*Attorney, Agent, or Firm*—Bacon & Thomas

[57] ABSTRACT

Compounds of general formula (I)

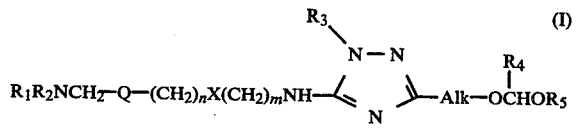

and physiologically acceptable salts and hydrates thereof in which $R_1$ and $R_2$ each represent methyl groups or together with the nitrogen atom to which they are attached form a pyrrolidino, piperidino or hexamethylenimino group;

$R_3$ represents hydrogen or methyl;

Alk represents a straight or branched alkylene chain of 1 to 6 carbon atoms;

$R_4$ represents a hydrogen atom and $R_5$ represents a $C_{1-4}$ alkyl group; or $R_4$ and $R_5$ together with the atoms to which they are attached form a tetrahydropyranyl ring; and either n is zero, X is oxygen, m is 3 or 4, and Q is a benzene ring linked through the 1- and 3- positions;

or n is 1, X is sulphur, m is 2, and Q is a furan ring linked through the 2- and 5- positions with optionally a methyl substituent on the carbon atom adjacent to the group $R_1R_2NCH_2$, or Q is a thiophene ring linked through the 2- and 4- positions with the group $R_1R_2NCH_2$ in the 2- position;

with the proviso that when Q is other than a benzene ring, $R_1$ and $R_2$ are methyl groups, are disclosed as having action as histamine $H_2$-antagonists.

12 Claims, No Drawings

PHARMACEUTICAL COMPOSITIONS CONTAINING COMPOUNDS HAVING ACTION ON HISTAMINE RECEPTORS

This application is a continuation of application Ser. No. 401,152 now abandoned, filed July 22, 1982.

This invention relates to pharmaceutical compositions containing heterocyclic derivatives having action on histamine receptors and their use in therapeutics.

The pharmaceutical compositions according to the invention contain as active ingredient certain heterocyclic derivatives which have potent activity as $H_2$-antagonists. These compounds which are more particularly described below, for example show inhibition of the secretion of gastric acid when this is stimulated via histamine receptors (Ash and Schild, Brit. J. Pharmacol. Chemother, 1966 27, 427). Their ability to do so can be demonstrated in the perfused rat stomach using the method described in British patent specification No. 1565966 modified by the use of sodium pentobarbitone (50 mg/kg) as anaesthetic instead of urethane, and in conscious dogs equipped with Heidenhain pouches using the method described by Black et al, Nature 1972 236, 385. Furthermore the compounds antagonise the effect of histamine on the contraction frequency of isolated guinea pig right atrium.

Compounds with histamine $H_2$-blocking activity any be used in the treatment of conditions where there is an advantage in lowering gastric acidity, particularly in gastric and pentic ulceration, as a prophylactic measure in surgical procedures, and in the treatment of allergic and inflammatory conditions where histamine is a known mediator. Thus they may be used for example, either alone or in combination with other active ingredients in the treatment of allergic and inflammatory conditions of the skin.

The present invention provides a pharmaceutical composition comprising at least one compound of the general formula (I)

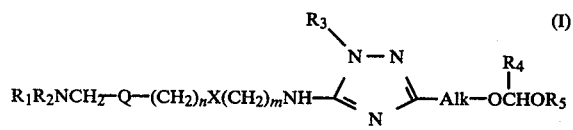

or a physiologically acceptable salt or hydrate thereof in which $R_1$ and $R_2$ each represent methyl groups or together with the nitrogen atom to which they are attached form a pyrrolidino, piperidino or hexamethylenimino group;

$R_3$ represents hydrogen or methyl;

Alk represents a straight or branched alkylene chain of 1 to 6 carbon atoms;

$R_4$ represents a hydrogen atom and $R_5$ represents a $C_{1-4}$ alkyl group; or $R_4$ and $R_5$ together with the atoms to which they are attached form a tetrahydropyranyl ring, i.e.

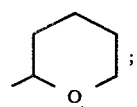

and either n is zero, X is oxygen, m is 3 or 4, and Q is a benzene ring linked through the 1- and 3-positions; or n is 1, X is sulphur, m is 2, and Q is a furan ring linked through the 2- and 5-positions with optionally a methyl substituent on the carbon atom adjacent to the group $R_1R_2NCH_2$, or Q is a thiophene ring linked through the 2- and 4-positions with the group $R_1R_2NCH_2$ in the 2-position;

with the proviso that when Q is other than a benzene ring, $R_1$ and $R_2$ are methyl groups, together with at least one inert pharmaceutically acceptable carrier or diluent.

Preferred active ingredients for use in the pharmaceutical compositions according to the present invention are compounds of the general formula (II) below. This group of compounds also forms part of the present invention, which thus also provides compounds of the general formula (II)

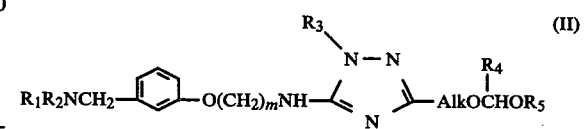

and physiologically acceptable salts and hydrates thereof, in which $R_1R_2N$ is a pyrrolidino, piperidino or hexamethylenimino ring; m is 3 or 4 and $R_3$, Alk, $R_4$ and $R_5$ are as defined in formula (I).

A particularly preferred group of compounds according to formula (II) are those in which $R_1R_2N$ is a piperidino ring, m is 3 and $R_3$ is methyl.

In the context of both formulae (I) and (II), more preferred compounds are those in which Alk represents methylene or ethylene, more preferably methylene and $R_4$ and $R_5$ together with the atoms to which they are attached form a tetrahydropyranyl ring, or $R_4$ represents hydrogen and $R_5$ represents methyl or more preferably ethyl.

More particularly preferred compounds of formula (II) are 1-methyl-N-[3-[3-(1-piperidinylmethyl)phenoxy]-propyl]-3-[(tetrahydro-2-pyranyl)oxymethyl]-1H-1,2,4-triazole-5-amine;

3-[(ethoxymethoxy)methyl]-1-methyl-N-[3-[3-(1-piperidinylmethyl)phenoxy]propyl]-1H-1,2,4-triazole-5-amine; and physiologically acceptable salts thereof.

The compounds of formula (I) may be used in the form of physiologically acceptable salts with inorganic and organic acids and the invention includes the compounds of formula (II) in the form of such salts. Particularly useful salts include hydrochlorides, hydrobromides, sulphates, methanesulphonates, acetates, maleates, succinates, citrates, tartrates, fumarates and benzoates. The compounds of formulae (I) and (II) and their salts may also form hydrates. The compounds of formula (I) may be used in the form of such hydrates and hydrates of the compounds of formula (II) should also be considered as part of the invention. The compounds of formulae (I) and (II) can exhibit tautomerism and the formulae are intended to cover all tautomers. Where optical isomers may exist the formulae are intended to cover all diastereoisomers and optical enantiomers.

The pharmaceutical compositions according to the invention, preferably containing the compound of formula (I) in the form of a salt, may be formulated for administration in any convenient way adapted for use in human or veterinary medicine. Such compositions may be formulated in a conventional manner using one or more pharmaceutically acceptable carriers or excipients. Such compositions may also contain if required other active ingredients e.g. H-antagonists.

Thus the compositions according to the invention may be formulated for oral, buccal, topical, parenteral or rectal administration. Oral administration is preferred.

For oral administration, the pharmaceutical compositions may take the form of, for example, tablets (including sustained release tablets) or capsules prepared by conventional means with pharmaceutically acceptable excipients such as binding agents (e.g. pregelatinised starch, polyvinylpyrrolidone or hydroxypropylmethylcellulose); fillers (e.g. lactose, microcrystalline cellulose or calcium phosphate); lubricants (e.g. magnesium stearate, talc or silica); disintegrants (e.g. potato starch or sodium starch glycollate); and/or wetting agents (e.g. sodium lauryl sulphate). The tablets may be coated by methods well known in the art. Oral liquid preparations may take the form of, for example, solutions, syrups or suspensions, or may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The compositions of the invention may be formulated in a manner suitable for parenteral administration by bolus injection or continuous infusion. Formulations for injection may be present in unit dosage form in ampoules, or in multi-dose containers, with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form for reconstitution with a soluble vehicle, e.g. sterile pyrogen-free water before use.

The compositions of the invention may also take the form of rectal compositions such as suppositories or retention enemas, e.g. containing conventional suppository bases such as cocoa butter or other glycerides.

For topical application, the compositions of the invention may take the form of ointments, creams, gels, lotions, powders or sprays which may be formulated in a conventional manner.

For internal administration a convenient daily dosage regime of the active ingredient of formula (I) would be 1 to 4 doses to the total of some 5 mg. to 1. g per day preferably 5 to 500 mg per day dependent upon the condition of the patient.

In describing the processes which may be used for preparing the compounds of formula (I) or intermediates useful in the preparation thereof any of $R_1$ to $R_5$, Q, n, X, m and Alk in the various formulae are as defined in formula (I) unless otherwise stated.

Compounds of formula (I) in which $R_4$ is hydrogen and $R_5$ represents a $C_{1-4}$ alkyl group may be prepared by reacting a hydroxyalkyltriazole of formula (III)

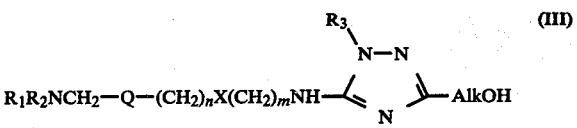

with an ether (IV)

$$LCH_2OR_5 \qquad (IV)$$

where L is a leaving group, e.g. halogen. The reaction may be carried out in a suitable solvent, e.g. tetrahydrofuran dimethylformamide or mixtures thereof, at a temperature of 20° to 100° C. preferably 60° to 80° C. in the presence of a base e.g. sodium hydride.

Compounds of formula (I) in which $CHR_4OR_5$ represents a tetrahydropyranyl ring may be prepared by reacting the hydroxyalkyltriazole (III) with dihydropyran in a solvent, e.g. dichloromethane or dimethylformamide, at low temperature, e.g. $-20°$ to $+10°$ C., in the presence of a catalyst, e.g. paratoluenesulphonic acid.

The hydroxyalkyltriazoles of formula (III) are described in British patent specification No. 2047238A and European patent specification No. 0027744.

Where the product of either of the above processes is a free base and a salt is required, the salt may be formed in a conventional manner. Thus, for example, a generally convenient method of forming the salts is to mix appropriate quantities of the free base and the acid in an appropriate solvent(s) e.g. an alcohol such as ethanol or an ester such as ethyl acetate.

The invention is illustrated by the following Examples:

EXAMPLE 1

1-Methyl-N-[3-[3-(1-piperidinylmethyl)phenoxy]-propyl]-3-[(tetrahydro-2-pyranyl)oxymethyl]-1H-1,2,4-triazole-5-amine. Compound with tartaric acid; (1:1)

Dihydropyran (1.4 ml) was added dropwise to a solution of 1-methyl-5-[[3-[3-(1-piperidinylmethyl)phenoxy]propyl]amino]-1H-1,2,4-triazole-3-methanol (2 g) and anhydrous p-toluenesulphonic acid (1.78 g) in dry dichloromethane (50 ml) at $-10°$. The reaction mixture was stirred at $-10°$ for 1 h and washed with saturated sodium carbonate solution (50 ml). The organic phase was dried, and evaporated to leave a yellow oil (2.8 g). A portion of this oil (2.0 g) was dissolved in ethyl acetate (30 ml) and treated with a saturated solution of tartaric acid in ethyl acetate to give the title compound as a white solid (1.52 g) m.p. 68°.

N.m.r. of free base (CDCl$_3$); 2.8, t, (1H); 3.0–3.3, m, (3H); 5.0–5.5, m, (2H); 5.5, d, (2H), 5.93, t, (2H); 5.9–6.5, m, (2H); 6.4, q, (2H); 6.5, s, (3H); 6.6, s, (2H); 7.6, m, (4H); 7.9, m, (2H); 8.0–8.7, m, (12H).

EXAMPLE 2

3-[(Ethoxymethoxy)methyl]-1-methyl-N-[3-[3-(1-piperidinylmethyl)phenoxy]propyl]-1H-1,2,4-triazole-5-amine A solution of 1-methyl-5-[[3-[3-(1-piperidinylmethyl)-phenoxy]propyl]amino]-1H-1,2,4-triazole-3-methanol (3.6 g) in dry tetrahydrofuran (30 ml) and dry dimethylformamide (3 ml), was added to a suspension of an 80% dispersion of sodium hydride in mineral oil (0.31 g), in dry tetrahydrofuran (10 ml). The suspension was heated under reflux for 0.5 h. and cooled to room temperature. Chloromethyl ethyl ether (1.0 ml) was added dropwise, and the suspension was heated at reflux for 1 h. The solvent was removed under reduced pressure, and the residual yellow oil was partitioned between aqueous sodium carbonate and ethyl acetate. The organic phase was chromatographed on silica using a mixture of dichloromethane:ethanol:0.880 ammonia (100:8:1) to give an oil (0.7 g). This oil was distilled to give the title compound (0.44 g) as a pale yellow oil b.p. 220°/0.06 mm Hg.

Found: C,62.8; H,8.5; N,17.1; $C_{22}H_{35}N_5O_3$ requires: C,63.2; H,8.5; N,16.8.

Examples of pharmaceutical compositions according to the invention are as follows:

(a) TABLETS

|  | mg/tablet | mg/tablet |
|---|---|---|
| Active ingredient | 20.0 | 40.0 |
| Microcrystalline cellulose BPC | 99.5 | 199.0 |
| Magnesium stearate B.P. | 0.5 | 1.0 |
| Compression weight | 120.0 | 240.0 |

The active ingredient is sieved through a 250 μm sieve, blended with the excipients and compressed using 6.5 mm and 8.0 mm diameter punches for the 20 and 40 mg strengths respectively. Tablets of other strengths may be prepared by increasing the compression weight and using punches to suit.

The tablets may be film coated with suitable film forming materials, e.g. methyl cellulose, ethyl cellulose or hydroxypropylmethyl cellulose, using standard techniques. Alternatively the tablets may be sugar coated.

(b) CAPSULES

|  | mg/capsule |
|---|---|
| Active ingredient | 20.0 |
| **Sta-Rx 1500-Starch | 79.5 |
| Magnesium Stearate B.P. | 0.5 |
| Fill weight | 100.0 |

**A form of directly compressible starch supplied by Colorcon Ltd, Orpington, Kent.

The active ingredient is sieved through a 250 μm sieve and blended with other materials. The mix is filled into No. 3 hard gelatin capsules using a suitable filling machine. Other doses may be prepared by increasing the fill weight and if necessary changing the capsule size to accommodate the increase.

(c) SUSTAINED RELEASE TABLETS

|  | mg/tablet |
|---|---|
| Active ingredient | 80.0 |
| *Cutina HR | 25.0 |
| Lactose B.P. | 142.5 |
| Magnesium Stearate B.P. | 2.5 |
| Compression weight | 250.0 |

*Cutina HR is a grade of microfine hydrogenated castor oil supplied by Sipon Products Ltd., London.

The active ingredient is sieved through a 250 μm sieve and blended with the Cutina HR and lactose. The mixed powders are moistened with Industrial Methylated Spirits 74 O.P., granules are made, dried, screened and blended with the magnesium stearate. The lubricated granules are compressed using 8.5 mm punches to produce tablets with a hardness of not less than 10 Kp (Schleuniger tester).

(d) INJECTION FOR INTRAVENOUS ADMINISTRATION

|  | % w/v |
|---|---|
| Active ingredient | 0.25 |
| Water for Injections BP to | 100.00 |

Sodium chloride may be added to adjust the tonicity of the solution and the pH may be adjusted to that of maximum stability using either dilute acid or alkali.

The solution is prepared, clarified and filled under nitrogen into appropriate sized ampoules sealed by fusion of the glass. The injection is sterilised by heating in an autoclave using one of the acceptable cycles. Alternatively the solution may be sterilised by filtration and filled into sterile ampoules under aseptic conditions.

(e) SYRUP

|  | mg/5 ml dose |
|---|---|
| Active ingredient | 20.0 mg |
| Sucrose | 2750.0 mg |
| Glycerine | 500.0 mg |
| Buffer | |
| Flavour | |
| Colour | as necessary |
| Preservative | |
| Distilled water to | 5.0 ml |

The active ingredient, buffer, flavour, preservative and colour are dissolved in some of the water. The remainder of the water is heated to approximately 80° C. and the sucrose is dissolved in this and cooled. The two solutions are mixed, adjusted to volume and clarified by filtration.

We claim:

1. A pharmaceutical composition for the treatment of conditions mediated through histamine $H_2$-receptors, comprising an effective amount for the treatment of the said condition of a compound of formula (I)

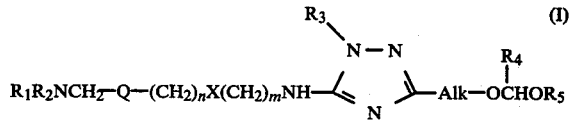

or a physiologically acceptable salt or hydrate thereof in which $R_1$ and $R_2$ each represent methyl groups or together with the nitrogen atom to which they are attached form a pyrrolidino, piperidino or hexamethylenimino group;

$R_3$ represents hydrogen or methyl;

Alk represents a straight or branched alkylene chain of 1 to 6 carbon atoms;

$R_4$ represents a hydrogen atom and $R_5$ represents a $C_{1-4}$ alkyl group; or $R_4$ and $R_5$ together with the atoms to which they are attached form a tetrahydropyranyl ring; and either n is zero, X is oxygen, m is 3 or 4, and Q is a benzene ring linked through the 1- and 3-positions; or n is 1, X is sulphur, m is 2, and Q is a furan ring linked through the 2- and 5-positions with optionally a methyl substituent on the carbon atom adjacent to the group $R_1R_2NCH_2$, or Q is a thiophene ring linked through the 2- and 4-positions with the group $R_1R_2NCH_2$ in the 2-position;

with the proviso that when Q is other than a benzene ring $R_1$ and $R_2$ are methyl groups, together with at least one pharmaceutically acceptable carrier or diluent.

2. A pharmaceutical composition for the treatment of conditions mediated through histamine $H_2$-receptors, comprising an effective amount for the treatment of the said condition of a compound of formula (II)

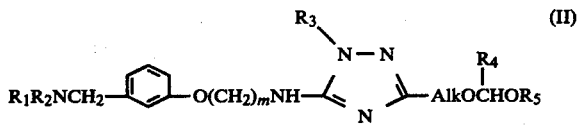

or a physiologically acceptable salt or hydrate thereof, in which $R_1R_2N$ is a pyrrolidino, piperidino or hexamethylenimino ring; m is 3 or 4; $R_3$ represents hydrogen or methyl; Alk represents a straight or branched alkylene chain of 1 to 6 carbon atoms; and $R_4$ represents a hydrogen atom and $R_5$ represents a $C_{1-4}$ alkyl group; or $R_4$ and $R_5$ together with the atoms to which they are attached form a tetrahydropyranyl ring.

3. A pharmaceutical composition according to claim 2 in which, in formula (II), $R_1R_2N$ is a piperidino ring, m is 3 and $R_3$ is methyl.

4. A pharmaceutical composition according to claim 1 in which, in formula (I); Alk represents methylene or ethylene and $R_4$ and $R_5$ together with the atoms to which they are attached form a tetrahydropyranyl ring or $R_4$ represents hydrogen and $R_5$ represents methyl or ethyl.

5. A pharmaceutical composition for the treatment of conditions mediated through histamine $H_2$-receptors comprising an effective amount of a compound selected from
1-methyl-N-[3-[3-(1-piperidinylmethyl)phenoxy]-propyl]-3-[(tetrahydro-2-pyranyl)oxymethyl]-1H-1,2,4-triazole-5-amine;
3-[(ethoxymethoxy)methyl]-1-methyl-N-[3-[3-(1-piperidinylmethyl)phenoxy]propyl]-1H-1,2,4-triazole-5-amine;

and physiologically acceptable salts thereof, together with at least one pharmaceutically acceptable carrier or diluent.

6. A pharmaceutical composition according to claim 1 in a form adapted for oral administration.

7. A compound of the formula (II)

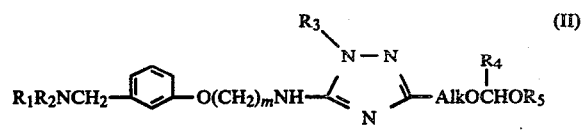

or a physiologically acceptable salt or hydrate therof in which $R_1R_2N$ is a pyrrolidino, piperidino or hexamethylenimino ring; m is 3 or 4; $R_3$ represents hydrogen or methyl; Alk represents a straight or branched alkylene chain of 1 to 6 carbon atoms; and $R_4$ represents a hydrogen atom and $R_5$ represents a $C_{1-4}$ alkyl group; or $R_4$ and $R_5$ together with the atoms to which they are attached form a tetrahydropyranyl ring.

8. A compound according to claim 7 in which $R_1R_2N$ is a piperidino ring, m is 3 and $R_3$ is methyl.

9. A compound according to claim 7 in which Alk represents methylene or ethylene and $R_4$ and $R_5$ together with the atoms to which they are attached form a tetrahydropyranyl ring or $R_4$ represents hydrogen and $R_5$ represents methyl or ethyl.

10. 1-Methyl-N-[3-[3-(1-piperidinylmethyl)phenoxy]-propyl]-3-[(tetrahydro 2-pyranyl)oxymethyl]-1H-1,2,4-triazole-5-amine; or
3-[(ethoxymethoxy)methyl]-1-methyl-N-[3-[3-(1-piperidinylmethyl)phenoxy]propyl]-1H-1,2,4-triazole-5-amine; or a physiologically acceptable salt thereof.

11. A method for the treatment of a condition mediated through histamine $H_2$-receptors which comprises administering to a patient an effective amount to alleviate said condition of a compound of formula (I) as defined in claim 1.

12. A method for the treatment of a condition mediated through histamine $H_2$-receptors which comprises administering to a patient an effective amount to alleviate said condition of a compound as claimed in claim 7.

* * * * *